United States Patent [19]

Sisto et al.

[11] Patent Number: 4,713,368
[45] Date of Patent: Dec. 15, 1987

[54] PEPTIDO-MIMETIC SUBSTANCES WITH HYPOTENSIVE ACTION

[75] Inventors: Alessandro Sisto; Antonio S. Verdini; Antonino Virdia; Giovanna De Luca; Giovanni Di Stazio; Vincenzo Politi, all of Rome, Italy

[73] Assignees: Eniricerche S.p.A., Milan; Polifarma S.p.A., Rome, both of Italy

[21] Appl. No.: 887,136

[22] Filed: Jul. 17, 1986

[30] Foreign Application Priority Data

Aug. 1, 1985 [IT] Italy ................. 21826 A/85

[51] Int. Cl.[4] .................. A61K 37/64; C07K 7/02
[52] U.S. Cl. ......................... 514/18; 514/19; 530/323; 530/331; 530/332
[58] Field of Search ............ 530/323, 331, 332; 514/18, 19

[56] References Cited

U.S. PATENT DOCUMENTS 4,619,916 10/1986 Di Stazio et al. ................. 514/18

Primary Examiner—Delbert R. Phillips
Assistant Examiner—Teresa D. Wessendorf
Attorney, Agent, or Firm—Hedman, Gibson, Costigan & Hoare

[57] ABSTRACT

Peptido-mimetic compounds of hypotensive action definable by the general formula:

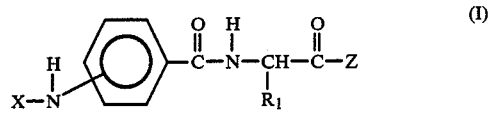

(I)

in which:

X represents the pyroglutamic acid residue or a

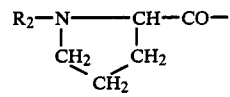

residue where $R_2$ represents a hydrogen atom, an alkyloxycarbonyl, an arylalkyloxycarbonyl or an acyl group with from 1 to 7 carbon atoms in the linear chain, $R_1$ represents the aromatic residue of L-phenylalanine, L-tyrosine or L-tryptophan, and Z represents a hydroxyl, hydroxyalkyl, amino or alkylamino group, and their salts and alkyl amides or esters.

12 Claims, No Drawings

PEPTIDO-MIMETIC SUBSTANCES WITH HYPOTENSIVE ACTION

This invention relates to peptido-mimetic compounds with hypotensive action, their salts and alkyl amides or esters, definable by the following formula

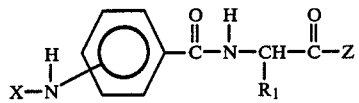

in which
X represents the pyroglutamic acid residue or a

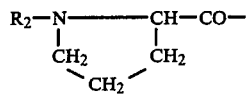

residue where $R_2$ represents a hydrogen atom, an alkyloxycarbonyl, an arylalkyloxycarbonyl or an acyl group with from 1 to 7 carbon atoms in the linear chain
$R_1$ represents the aromatic residue of L-phenylalanine, L-tyrosine or L-tryptophan, and
Z represents a hydroxyl, hydroxyalkyl, amino or alkylamino group.

The technical and patent literature describes numerous peptide compounds useful in the treatment of hypertension. Italian patent application No. 49574 A/83 describes and claims a class of tripeptides of hypotensive action characterised in that the N-terminal α-amino acid is pyroglutamic acid, the C-terminal α-amino acid is L-tryptophan and the amino acid in position 2 of the peptide chain is a natural α-amino acid.

When said peptides are tested on normo-tensive rats they exercise a hypotensive action and can be used as compounds in the treatment of hypertension.

However, it has been found that the biological activity of said compounds decays rapidly with time, thus limiting their use in therapy.

The reasons for this limitation are due to the presence in the tripeptide chain of sites in which the peptide bond between adjacent amino acids is easily hydrolised by peptidase enzymes. Consequently, the object of the present invention is to provide compounds of hypotensive activity which are free or substantially free from the aforesaid drawbacks.

The present invention is based on the unexpected discovery that only the first and last amino acid of the tripeptide are directly involved in pharmalogical activity, whereas the second amino acid residue functions as a suitable spacer.

In accordance with this, it has been found that by replacing the amino acid in position 2 of the tripeptide chain with an aromatic group, compounds are obtained in which the in vivo biological activity is unaltered, and said activity is maintained with time. Consequently an object of the present invention is to provide peptido-mimetic compounds of hypotensive activity having a greater in vivo stability to the hydrolytic action of peptidase enzymes.

A further object of the present invention is the use of said compounds in the treatment of hypertensive states.

These objects are attained according to the present invention by peptido-mimetic compounds of hypotensive activity definable by the general formula:

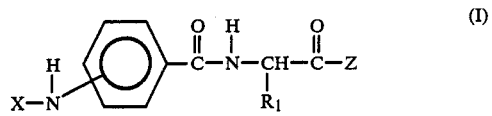

in which
X represents the pyroglutamic acid residue or a

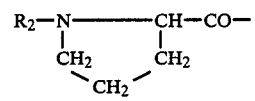

residue where $R_2$ represents a hydrogen atom, an alkyloxycarbonyl, an arylalkyloxycarbonyl or an acyl group with from 1 to 7 carbon atoms
$R_1$ represents the aromatic residue of L-phenylalanine, L-tyrosine or L-tryptophan, and
Z represents a hydroxyl, hydroxyalkyl, amino or alkylamino group, and their pharmaceutically acceptable salts and alkyl amides or esters.

Particularly suitable for this purpose are peptido-mimetic compounds of formula (I) in which X is the pyroglutamic acid residue.

The presence of the aromatic group in position 2 of the linear chain of said peptido-mimetic compounds not only gives greater rigidity to the molecule but also increases its hydrophobicity, thus allowing greater interaction of the two terminal amino acid residues with the receptor.

Aminobenzoic acid is used as the aromatic group.

The bond position between the amino group and the benzyl residue is not limitative of the invention.

In accordance with the present invention, the compounds of formula (I) are prepared by condensation induced by dicyclohexyl carbodiimide (DCI) and N-hydroxy-benzotriazole (HOBt) between the compound

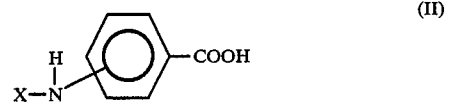

where X has the aforesaid meaning, and the amino acid derivative

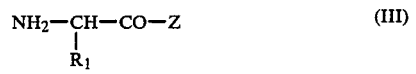

where $R_1$ and Z have the aforesaid meaning.

The condensation reaction is carried out by reacting the compound (II) with DCI and HOBt at a temperature of between $-10°$ C. and $+10°$ C. for a period of about 30 minutes, and at ambient temperature ($20°-25°$ C.) for a further 30 minutes.

Compound (III) is then added to the reaction mixture, and the temperature maintained at $20°-25°$ C. for a period of about two hours.

The precipitated dicyclohexylurea is separated from the reaction mixture by filtration, and the solution is evaporated to dryness. The solid residue thus obtained is re-suspended in ethyl acetate and successively extracted with a 5% aqueous NaHCO$_3$ solution, an aqueous 0.1N hydrochloric acid solution and finally a saturated NaCl solution.

The organic extract is dried with magnesium sulphate, filtered and evaporated to dryness under vacuum.

The solid residue is taken up and triturated with n-hexane. The required product is finally separated from the reaction mixture by filtration, and dried under vacuum.

By operating in this manner compounds (I) are obtained with a yield of between 68% and 72%.

In accordance with the present invention, the amino acid derivative (II) is prepared by condensation induced by DCI and N-hydroxysuccinimide (HONSu) between the amino acid residue

X—HO where X has the aforesaid meaning, and aminobenzoic acid

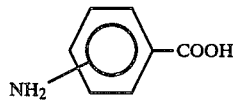

in which the amino group is bonded in the para, ortho or meta position.

The procedure is typically carried out by suspending the amino acid derivative X—OH in dimethylformamide, cooled previously to 0° C., and adding to the agitated solution the N-hydroxysuccinimide and the dicyclohexylcarbodiimide dissolved in dimethylformamide. The mixture obtained in this manner is maintained at a temperature of between −10° C. and +10° C. under mild agitation for a period of between 10 and 15 hours.

Generally, the procedure is carried out at a temperature of about −4° C. for a period of about 12 hours.

On termination of the reaction, the precipitated dicyclohexylurea is removed from the reaction mixture by filtration, and the solution is evaporated to dryness.

The solid residue thus obtained is taken up in tetrahydrofuran, filtered and then added to a solution containing aminobenzoic acid and N-methylmorpholine dissolved in tetrahydrofuran.

The condensation reaction is conducted by maintaining the mixture obtained in this manner at a temperature of between −10° C. and +10° C. under agitation for a period of between 10 and 15 hours. The solvent is then evaporated to dryness and the oily residue treated with an aqueous 5% sodium chloride solution.

The reaction mixture is filtered and the residue dried to obtain the condensation product in the form of a white powder.

On termination of the condensation reactions, any temporary protector groups used for protecting the functional groups present in the amino acid derivatives and chosen from those known to an expert of the art are removed.

The product is then isolated by known methods such as extraction, countercurrent distribution, precipitation, crystallisation or chromatography.

Product identity is verified by nuclear magnetic resonance spectrometry for proton analysis ($^1$Hn.m.r).

The purity of the compounds of the present invention is measured by reverse phase high pressure liquid chromatography (RP-HPLC). Typically, the procedure uses a Perkin Elmer chromatograph with a 250×4 mm HI-BAR ® COLUMN and Lichrosorb ® RP-18 10μ (Merck) filling, using as mobile phase a mixture (A) of 90% CH$_3$CN, 0.1% trifluoroacetic acid (TFA) and water, and a mixture (B) of 10% CH$_3$CN, 0.1% TFA and water.

Elution uses a linear gradient over 25 minutes from 20% to 65% of A.

The purity of the compounds of formula (I) is also measured by silica gel thin layer chromatography (TLC) using the following eluent systems: n-butanol:acetic acid:water (4:1:1) (BAW) and chloroform:methanol:acetic acid (85:10:5) (CMA).

The hypotensive activity of the compounds of the present invention is tested on the arterial pressure of normo-tensive male rats of weight 200-300 g anesthetised with ethylurethane (1.75 g/kg/intraperitoneal administration).

After cannulating the trachea, the right carotid is isolated and connected by cannula to a Hewlett-Packard model 1280 pressure transducer, whereas the arterial flow is recorded in the isolated left carotid by a Biotronex ® model BL 610 electromagnetic flow meter.

Other parameters, recorded on a Hewlett-Packard model 8824-C polygraph, are the pressure variation with time (dp/dt), the electrocardiogram (ECG) and the heartbeat per minute (BPM). The compounds tested in this manner induce a gradual and durable hypotensive effect which at a dose of 0.2 mg/kg of body weight attains a delta value for the diastolic arterial pressure of 30 mmHg to 35 mmHg and for the systolic arterial pressure a delta value of 30 mmHg to 40 mmHg.

It was also found that the preferable daily dose per kg of body weight in terms of the pure compound is as follows:
from 2 to 10 mg by intravenous administration
from 10 to 50 mg by intramuscular administration
from 100 to 300 mg by oral administration.

The experimental examples given hereinafter are illustrative of the invention but not limitative thereof.

EXAMPLE 1

Synthesis of N-(pyroglutamyl)-p-aminobenzoic acid (Glp-pAba-OH)

2.6 g (20 mmoles) of L-pyroglutamic acid are dissolved in 40 ml of dimethylformamide (DMF), and 2.53 g (22 mmoles) of N-hydroxysuccinimide (HONSu) and 4.12 g (20 mmoles) of dicyclohexylcarbodiimide (DCI) dissolved in 15 ml of DMF are added to the solution cooled to 0° C. and under strong agitation.

The agitated reaction mixture is maintained at a temperature of −4° C. for 12 hours, filtered to eliminate the precipitated dicyclohexylurea (DCU) and then evaporated to dryness.

The solid residue thus obtained is taken up in 50 ml of tetrahydrofuran, filtered and added to a solution containing 2.74 g (20 mmoles) of p-aminobenzoic acid and 2 ml of N-methylmorpholine (NMM) in 20 ml of tetrahydrofuran.

The reaction mixture is kept under agitation at a temperature of 0° C. for 12 hours.

On termination of this time period, the solvent is evaporated to dryness, and the oily residue is triturated with 50 ml of an aqueous 5% sodium chloride solution.

The product is isolated by filtration and dried under vacuum. 3.51 g (71%) of product Glp-pAba-OH are obtained in the form of a white powder which shows no traces of impurity on chromatographic analysis (TLC and HPLC).

The $^1$Hn.m.r spectrum confirms the molecular structure.

EXAMPLE 2

Synthesis of the methyl ester of N-(pyroglutamyl)p-aminobenzoyl tryptophan (Glp-pAba-Trp-Ome)

2.044 g (14 mmoles) of N-hydroxy-benzotriazole (HOBt) and 2.47 g (12 mmoles) of DCI are added to 25 ml of a solution of DMF containing 2.97 g (12 mmoles) of Glp-pAba-OH, cooled to 0° C. The solution thus obtained is kept under agitation at 0° C. for 30 minutes, and at ambient temperature (20°–25° C.) for a further 30 minutes.

On termination of this time period, 25 ml of DMF containing 2.80 g (11 mmoles) of the hydrochloride of L-tryptophan methyl ester (HCl-TrpOMe) and 1.02 ml (11 mmoles) of NMM are added.

The condensation reaction is conducted at ambient temperature for a period of 2 hours.

On termination, the reaction mixture is filtered to remove the precipitated DCU and is then evaporated to dryness.

The solid residue thus obtained is taken up in 100 ml of ethyl acetate (EtOAc) and extracted three times with 25 ml each time of an aqueous 5% NaHCO$_3$ solution, three times with 25 ml each time of a 0.1N hydrochloric acid solution, and finally three times with 25 ml each time of a saturated NaCl solution.

The organic extract is dried with magnesium sulphate, filtered and then evaporated to dryness.

The solid residue thus obtained is triturated with 100 ml of n-hexane, filtered and then dried under vacuum. 3.54 g (72%) of a colourless microcrystalline product are obtained which shows no traces of impurity on chromatographic analysis (TLC and HPLC).

The $^1$Nh.m.r spectrum confirms the molecular structure.

EXAMPLES 3 AND 4

Synthesis of N-(pyroglutamyl)p-aminobenzoyl-phenylalanine methyl ester (Glp-pAba-Phe-OMe) and of N-(pyroglutamyl)p-aminobenzoyltyrosine methyl ester (Glp-pAba-Tyr-OMe)

The procedure of Example 2 is followed, using for the condensation reaction with Glp-pAba-OH 2.26 g (11 mmoles) of the hydrochloride of L-phenylalanine methyl ester and 2.31 g (11 mmoles) of the hydrochloride of L-tyrosine methyl ester respectively.

On termination of the reactions 3.5 g (78%) of Glp-pAba-Phe-OMe and 3.8 g (81%) of Glp-pAba-Tyr-OMe are obtained.

The compounds show no traces of impurity on chromatographic analysis (TLC and HPLC), and the $^1$Hn.m.r spectrum confirms the molecular structure.

EXAMPLE 5

Synthesis of N-(acetyl-prolyl)p-aminobenzoic acid (Ac-Pro-pAba-OH)

The procedure if Example 1 is followed, using 3.14 g (20 mmoles) of N-acetyl-L-proline, 2.53 g (22 mmoles) of HONSu and 4.12 g (20 mmoles) of dicyclohexylcarbodiimide.

4.7 g (85%) of the compound Ac-Pro-pAba-OH are obtained, showing no traces of impurity on chromatographic analysis (TLC and HPLC). The $^1$Hn.m.r spectrum confirms the molecular structure.

EXAMPLE 6

Synthesis of N-(acetyl-prolyl)p-aminobenzoyl-tryptophan methyl ester (Ac-Pro-pAba-Trp-OMe)

The procedure of example 2 is followed, using 4.1 g (15 mmoles) of Ac-Pro-pAba-OH and 3.81 g (15 mmoles) of the hydrochloride of L-tryptophan methyl ester (HCl. Trp-OMe).

6.1 g (79.5%) of a colourless microcrystalline product are obtained, which shows no traces of impurity on chromatographic analysis (TLC and HPLC).

EXAMPLES 7 AND 8

Synthesis of N-(acetyl-prolyl)p-aminobenzoyl-phenylalanine methyl ester (Ac-Pro-pAba-OMe) and of N-(acetyl)-prolyl)p-aminobenzoyltyrosine methyl ester (Ac-Pro-pAba-Tyr-OMe)

The procedure of Example 6 is followed, using in the condensation reaction 3.08 g (15 mmoles) of the hydrochloride of L-phenylalanine methyl ester and 3.47 g (15 mmoles) of the hydrochloride of L-tyrosine methyl ester respectively.

On termination of the reaction, 5.1 g (73%) of Ac-Pro-pAba-Phe-OMe and 5.8 g (78%) of Ac-Pro-pAba-Tyr-OMe are obtained. The products show no traces of impurity on chromatographic analysis (TLC and HPLC), and the $^1$Hn.m.r spectrum confirms the molecular structure.

We claim:

1. Peptido-mimetic compounds of hypotensive action definable by the general formula:

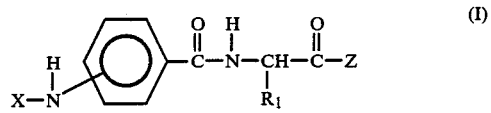

in which

X represents the pyroglutamic acid residue or a

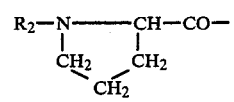

residue where R$_2$ represents a hydrogen atom, an alkyloxycarbonyl, an arylalkyloxycarbonyl or an acyl group with a maximum of between 1 and 7 carbon atoms in the linear chain R$_1$ represents the aromatic residue of L-phenylalanine, L-tyrosine or L-tryptophan, and Z represents a hydroxyl, hydroxyalkyl, amino or alkylamino group.

2. The compound N(pyroglutamyl)-aminobenzoyl-tryptophan methyl ester

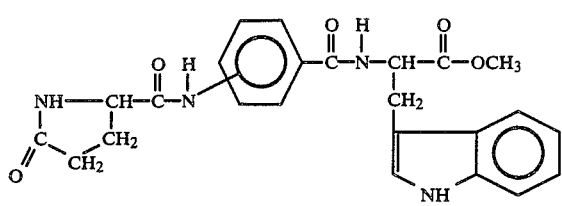

in which the α-amino acids have L configuration.

3. The compound N(pyroglutamyl)-aminobenzoylphenylalanine methyl ester

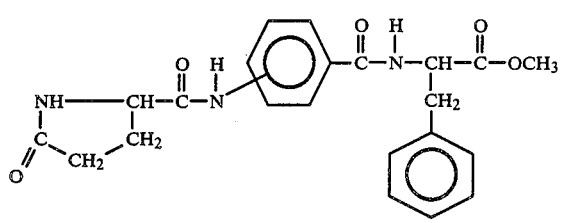

in which the α-amino acids have L configuration.

4. The compound N(pyroglutamyl)-aminobenzoyltyrosine methyl ester

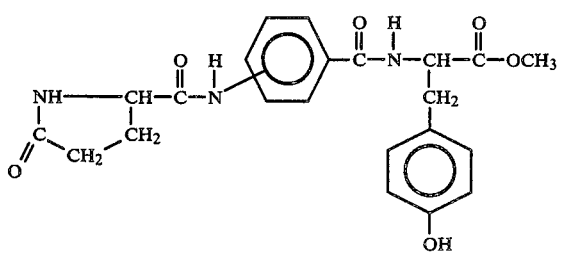

in which the α-amino acids have L configuration.

5. The compound N(prolyl)-aminobenzoyltryptophan methyl ester

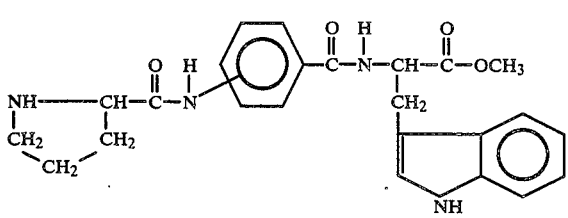

in which the α-amino acids have L configuration.

6. The compound N(prolyl)-aminobenzoylphenylalanine methyl ester

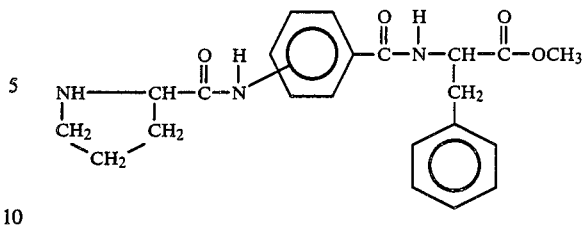

in which the α-amino acids have L configuration.

7. The compound N(prolyl)-aminobenzoyltyrosine methyl ester

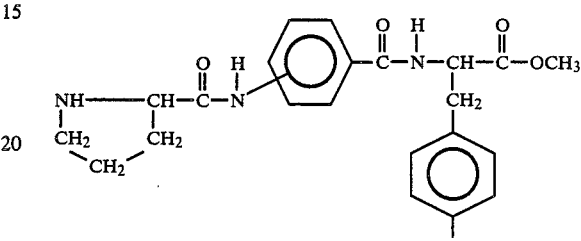

in which the α-amino acids have L configuration.

8. The compound N(acetylprolyl)-aminobenzoyltryptophan methyl ester

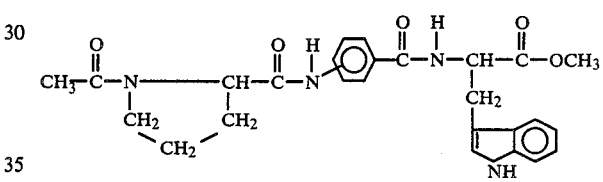

in which the α-amino acids have L configuration.

9. The compound N(acetylprolyl)-aminobenzoylphenylalanine methyl ester

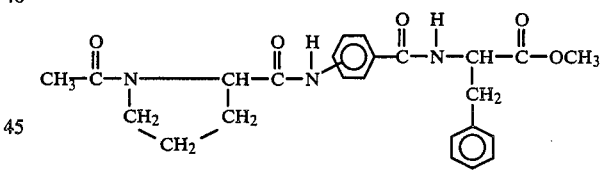

in which the α-amino acids have L configuration.

10. The compound N(acetylpropyl)-aminobenzoyltyrosine methyl ester

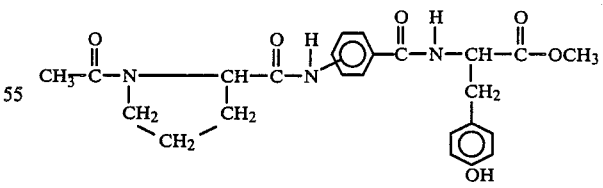

in which the α-amino acids have L configuration.

11. A composition containing a therapeutically effective quantity of a compound claimed in claim 1 and a pharmaceutically compatible quantity of an excipient.

12. A method for reducing the blood pressure of mammals, comprising administering to a hypertensive mammal a therapeutically effective quantity of a compound of formula (I) or a pharmaceutical composition comprising said compounds.

* * * * *